(12) United States Patent
Zhao

(10) Patent No.: US 9,254,221 B2
(45) Date of Patent: Feb. 9, 2016

(54) HEART-TYPE CIRCULATION DEVICE

(71) Applicant: Henglai Zhao, Shandong (CN)

(72) Inventor: Henglai Zhao, Shandong (CN)

( * ) Notice: Subject to any disclaimer, the term of this patent is extended or adjusted under 35 U.S.C. 154(b) by 4 days.

(21) Appl. No.: 14/236,074

(22) PCT Filed: May 10, 2013

(86) PCT No.: PCT/CN2013/075435
§ 371 (c)(1),
(2) Date: Jan. 30, 2014

(87) PCT Pub. No.: WO2013/166982
PCT Pub. Date: Nov. 14, 2013

(65) Prior Publication Data
US 2015/0075644 A1   Mar. 19, 2015

(30) Foreign Application Priority Data

May 11, 2012   (CN) .......................... 2012 1 0144484

(51) Int. Cl.
*E03B 7/07* (2006.01)
*A61F 7/00* (2006.01)
*A47G 9/02* (2006.01)
(Continued)

(52) U.S. Cl.
CPC ............. *A61F 7/0097* (2013.01); *A47C 21/048* (2013.01); *A47G 9/0215* (2013.01); *F04B 17/04* (2013.01); *F04B 23/02* (2013.01); *F04B 43/04* (2013.01); *F24H 1/101* (2013.01); *F24H 9/14* (2013.01); *A61F 2007/0054* (2013.01); *F24H 2250/08* (2013.01); *Y10T 137/6606* (2015.04)

(58) Field of Classification Search
CPC ................... Y10T 137/2213; B01L 3/502738; F16K 99/0042; F16K 99/0046; F16K 2099/0084; F16K 2099/0098; A61F 7/0097; A61F 2007/0054

USPC ........ 137/563, 564, 831; 251/129.01, 129.02, 251/129.17
See application file for complete search history.

(56) References Cited

U.S. PATENT DOCUMENTS 2,119,740 A * 6/1938 Fellows et al. ................. 137/563
3,942,559 A * 3/1976 Kranz et al. ................... 137/831
(Continued)

*Primary Examiner* — John K Fristoe, Jr.
*Assistant Examiner* — Reinaldo Sanchez-Medina
(74) *Attorney, Agent, or Firm* — Wiersch IP lAW

(57) ABSTRACT

A heart-type circulation device comprises a power system, a cover plate (16), an elastic plate (5), a pressing contact ring (6), a water inlet (13), a check valve A (9), a self-pressing liquid storage tank (12), a check valve B (10), a water outlet (11), and a pipeline (17). The elastic plate (5) is disposed above the power system, the pressing contact ring (6) is disposed on the periphery of a bottom surface of the elastic plate (5), and the pressing contact ring (6), the elastic plate (5), and the cover plate (16) are fixedly connected in sequence from bottom to top. The water inlet (13) and the water outlet (11) are in communication with each other between the cover plate (16) and the elastic plate (5) via the cover plate (16) respectively. The water inlet (13), the check valve A (9), the self-pressing liquid storage tank (12), the check valve B (10), and the water outlet (11) are connected in sequence via the pipeline (17), wherein the direction of the check valve A (9) is the direction of a fluid flowing to the cover plate (16), and the direction of the check valve B (10) is the direction of the fluid flowing out of the cover plate (16). The space where the whole pipeline (17) is in communication with the self-pressing liquid storage tank (12) is filled up with a liquid. The heart-type circulation device has a simple structure, makes no noise, and has no leakage and a low maintenance rate, and is energy-saving, environment-friendly, green and efficient.

8 Claims, 7 Drawing Sheets

(51) Int. Cl.
*A47C 21/04* (2006.01)
*F24H 1/10* (2006.01)
*F24H 9/14* (2006.01)
*F04B 17/04* (2006.01)
*F04B 23/02* (2006.01)
*F04B 43/04* (2006.01)

(56) References Cited

U.S. PATENT DOCUMENTS

| | | | |
|---|---|---|---|
| 6,334,761 B1 * | 1/2002 | Tai et al. | 417/413.3 |
| 8,240,636 B2 * | 8/2012 | Smith | 251/129.19 |
| 2011/0315252 A1 * | 12/2011 | Oh | 137/564 |

* cited by examiner

HEART-TYPE CIRCULATION DEVICE

FIELD OF THE INVENTION

The present invention relates to a new circulation device, specifically relates to a heart-type circulation device.

BACKGROUND OF THE INVENTION

Electric blanket used daily is provided with resistance wire which is distributed in the inside of the blanket uniformly, and generates heat by heating the resistance wire. However, its disadvantage is also obviously, a large number of the resistance wires inside of the electric blanket generate high electromagnetic radiation, which could affect the human health seriously. In addition, the electric blanket further makes the people feel dry easily, and has electric leak risk, and results the fire easily if it has been electrified for a long time.

Even if with a circulation plumbing pad, the existing circulation device also uses the centrifugal pump mainly, that is, an impeller is driven by a pump shaft to rotate, that has an action on the fluid between the blades, and the fluid is thrown to the periphery of the pad under the act of the centrifugal force. This kind of circulation device has the following defects:

1. It has loud noise. When the blade is rotating, it will generate a loud noise which will affect the people's sleeping.
2. It usually has leakage and high repair rate. Because the blade always has been kept rotating in the rotate state, thus the seal of the blade can be damaged by attrition easily, the leaked water would soak the pads and clothing, which might cause a great inconvenience to usage.
3. It consumes high energy. Because the motor always drive the blade to rotate, thus it will always consume energy when it is turned on by a long time for warm, the energy saving performance is poor.

SUMMARY OF THE INVENTION

To overcome the above defects, the present invention provides a heart-type circulation device which has a simple structure, without an noise, and has no leakage and low repair rate, and is energy-saving and environment-friendly, green and efficient. The device is used in the pad which replaces the existing electric blanket and plumbing pad, that can provide comfort, health and safety for people.

The heart-type circulation device of the present invention, comprises a power system, a cover plate, an elastic plate, a pressing compact ring, a water inlet, a check valve A, a self-pressing liquid storage tank, a check valve B, a water outlet and a pipeline; in which the elastic plate is disposed above the power system, the pressing compact ring is disposed on the periphery of the bottom surface of the elastic plate, the pressing compact ring, the elastic plate and the cover plate are fixedly connected one by one in sequence from bottom to top; the water inlet and the water outlet are lead to the place between the cover plate and the elastic plate through the cover plate respectively; the water inlet, the check valve A, the self-pressing liquid storage tank, the check valve B and the water outlet are connected one by one in sequence by the pipeline, in which the direction of the check valve A is the same with the direction of liquid flowing to the cover plate, and the direction of the check valve B is the same with the direction of the liquid flowing out of the cover plate; the space where the whole pipeline connected with the tank is filled up with liquid.

Under the normal conditions, the whole pipeline is filled with liquid, the cover plate and the elastic plate are not fitted with each other, a reservoir space is formed between the both of them. In working conditions, the power system first moves upward to flat-pressing the whole elastic plate so as to fit the elastic plate with the cover plate, thus the reservoir space between the both gradually reduces to zero, thereby the liquid in the reservoir space flows through the check valve B by the water outlet to flow into the self-pressing liquid storage tank. The self-pressing liquid storage tank stores the liquid, the function of which is: when the liquid therein is increased, the liquid itself will be suffered pressure, at the same time, the power system is activated to release the pressure of the power system suffered by the elastic plate, the liquid in the pipeline only pass through the check valve A to flow into the water inlet from the self-pressing liquid storage tank under the pressure of the self-pressing liquid storage tank and the gravity of the liquid itself, finally, it flows back to the reservoir space between the cover plate and the elastic plate. Thus, one water cycle is completed. The above water cycle is performed repeatedly under the action of the power system.

The heart-type circulation device described by the present invention has a simple structure, which clever use the gravity of the liquid and the pressure of the self-pressing liquid storage tank, and combines with the check valve, the liquid cycle will be completed by just applying a minor power, the advantages are:

1. It makes no noise. Because the present invention does not make the impeller rotate in high-speed, and does not have any parts with noise, thus it is quiet, green and efficient.
2. It has no leakage and with low repair rate. The structure of the present invention leads to the seals thereof to wear small and difficult to generate a leakage.

It consumes less power, and it is energy-efficient. Most of the power consumed by the present invention is used to complete the liquid cycle, and the power for overcoming the resistance which is wasted is small, thus it has low loss and obtains high efficiency.

To achieve better effect, the present invention can further take the following measures:

1. The self-pressing liquid storage tank of the present invention is made of rigid material, liquid is not filled up with therein, the space above the liquid surface is air; or the self-pressing liquid storage tank is made of elasticity material, liquid is filled up with therein. In this manner, when the liquid in the pipeline is pressed into the self-pressing liquid storage tank, the air or the elasticity material of the self-pressing liquid storage tank is extruded, the liquid flowed into the self-pressing liquid storage tank will be suffered pressure of it, and coordinated with other components of the device to complete the whole liquid cycle.
2. The present invention further comprises a heating pipe which is connected with the pipeline. Because the role of the heating pipe, the temperature of the liquid in the pipeline will be elevated, and it has an advantage of comfortable and healthy to dispose the pipeline on the pad, it can prevent the leakage, and obtains higher safety.
3. The cover plate of the present invention is made of magnetic material, the power system comprises a core, a coil, an insulation plate and a pulse power, in which the coil is wound on the core, the both end of the coil are connected with the pulse power, and the insulation plate is disposed on the top of the core. The above structure uses the pulse power which makes the devise has not always been energized, this is enough for the plumbing heating pad, thus it consumes less power and is energy-efficient.

When working, the pulse power supplies pulse current to the coil, and when the pulse current passes through the coil, the core will generate magnetic field, the magnetic field pass through the elastic plate to attract the cover plate, thereby the elastic plate is fitted with the cover plate, when the pulse current does not pass through the coil, the magnetic field of the core is disappeared, the reservoir space will be formed between the elastic plate and the cover plate.

The insulation plate is used for isolating the coil from the outside world.

The frequency of the pulse power is adjustable. When the frequency is increased, the cycle speed of the liquid in the pipeline is accelerated.

4. The shape of the above core is two concentric cylinders, in which the inner cylinder is solid which is disposed on the center of the outer cylinder, and the outer cylinder is hollow, and the core is in an E-type cross-sectional shape; the coil is wound on the inner cylinder; the insulation plate is an annulus, and the center hole of which is matched with the core, the connection between the both are sealed and their top surfaces are in the same surface.

When the coil is energized, the inner cylinder of the core generates magnetic line of force, the arrangement of the magnetic line of force forms a closed curve in the path of the inner cylinder to pass through the cover plate and the outer cylinder, thereby the whole core will generates magnetic force to generate attraction force to the cover plate.

5. A concave platform is disposed on the periphery of the core of the power system, the concave platform is adapted to the pressing compact ring; the power system further comprises several limit stops, the section of the limit stop is groove profile, the cover plate and the concave platform are clipped in the groove, the bottom of the limit stop is fixed on the underside of the concave platform, the top of the aid limit stops are provided with adjustment screws. The distance of the cover plate can be adjusted by the adjusting screws, thereby a comfortable distance can be maintained between the cover plate and the top surface of the core to ensure the elastic plate and the cover plate can be fitted and separated from each other.

6. The depth of the concave platform of the core is less than the thickness of the pressing compact ring. In this manner, when the cover plate is fitted with the elastic plate, the pressure of the whole cover plate is undertaken by the concave platform, thereby the abrasion of the elastic plate from the core or the insulation plate is reduced.

7. The present invention further comprises several springs which are disposed between the concave platform and the pressing compact ring. When the electric current of the coil is equaled to zero, the pressure suffered by the pressing plate is removed, the spring which was under the compress state starts to stretch, the cover plate moves upward, and the water will continually flow into the reservoir space with the movement of the cover plate. In this manner, in the case of not need to generate a higher pressure, can be, the liquid can continually flow into the water inlet via the check valve A depending on its gravity, so the reservoir space of the self-pressing liquid storage tank is formed more easily.

8. The power system further is consisted of a cam mechanism or cylinder mechanism. The elastic plate is extruded by the unique motion of the cam or the repeated motion of the cylinder, thereby the fit and separation of the elastic plate and the cover plate can be obtained.

9. The check valve A and the check valve B are mechanical valves or solenoid valves.

The work principle of the circulation device is similar with the human heart. In which, the reservoir space is equivalent to the ventricular, the self-pressing liquid storage tank is equivalent to the atrium, and the pipeline is equivalent to the vein. The pressure in the pipeline is adapted to the human pressure by adjusting the pressure of the check valve A. The working frequency is adapted to the frequency of the human pulse by adjusting the power system. The present invention is also expected to be used for the human heart except for using for blankets, mattresses and warm equipment, the study of the details of the application to the human heart is certainly to be investigated by the medical field.

1. Core; 2. Coil; 3. Pulse power; 4. Insulation plate; 5. Elastic plate; 6. Pressing compact ring; 7. Screw; 8. Heating pipe; 9. Check valve A; 10. Check valve B; 11. Water outlet; 12. Self-pressing liquid storage tank; 13. Water inlet; 14. Reservoir space; 15. Concave platform; 16. Cover plate; 17. Pipeline; 18. Limit stop; 19. Limit screw; 20. Spring.

DETAILED DESCRIPTION OF THE PREFERRED EMBODIMENTS

Hereafter, the heart-type circulation device of the present invention will be described in detail by referring to FIGS. 1-4.

The heart-type circulation device of the present invention comprises a circulation system and a power system.

Figure 3:
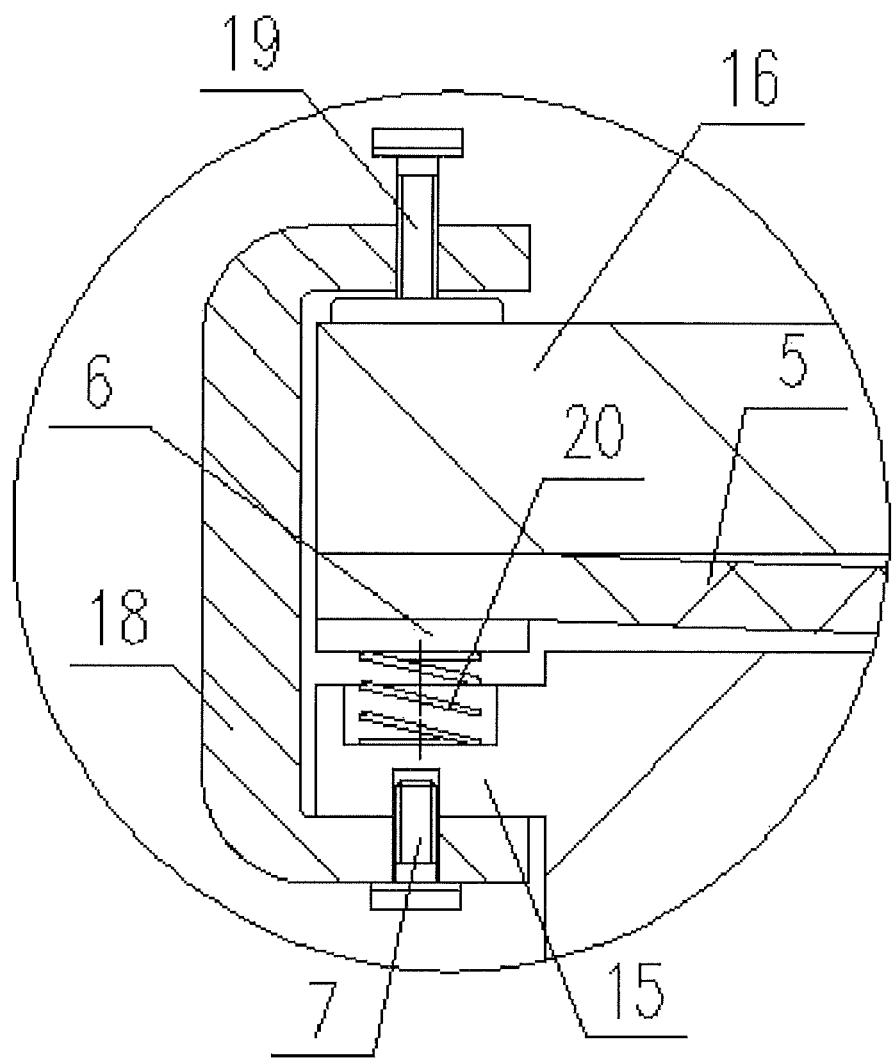
FIG. 3 is an enlarged diagram illustrating the spring position of FIG. 1.
Figure 4:
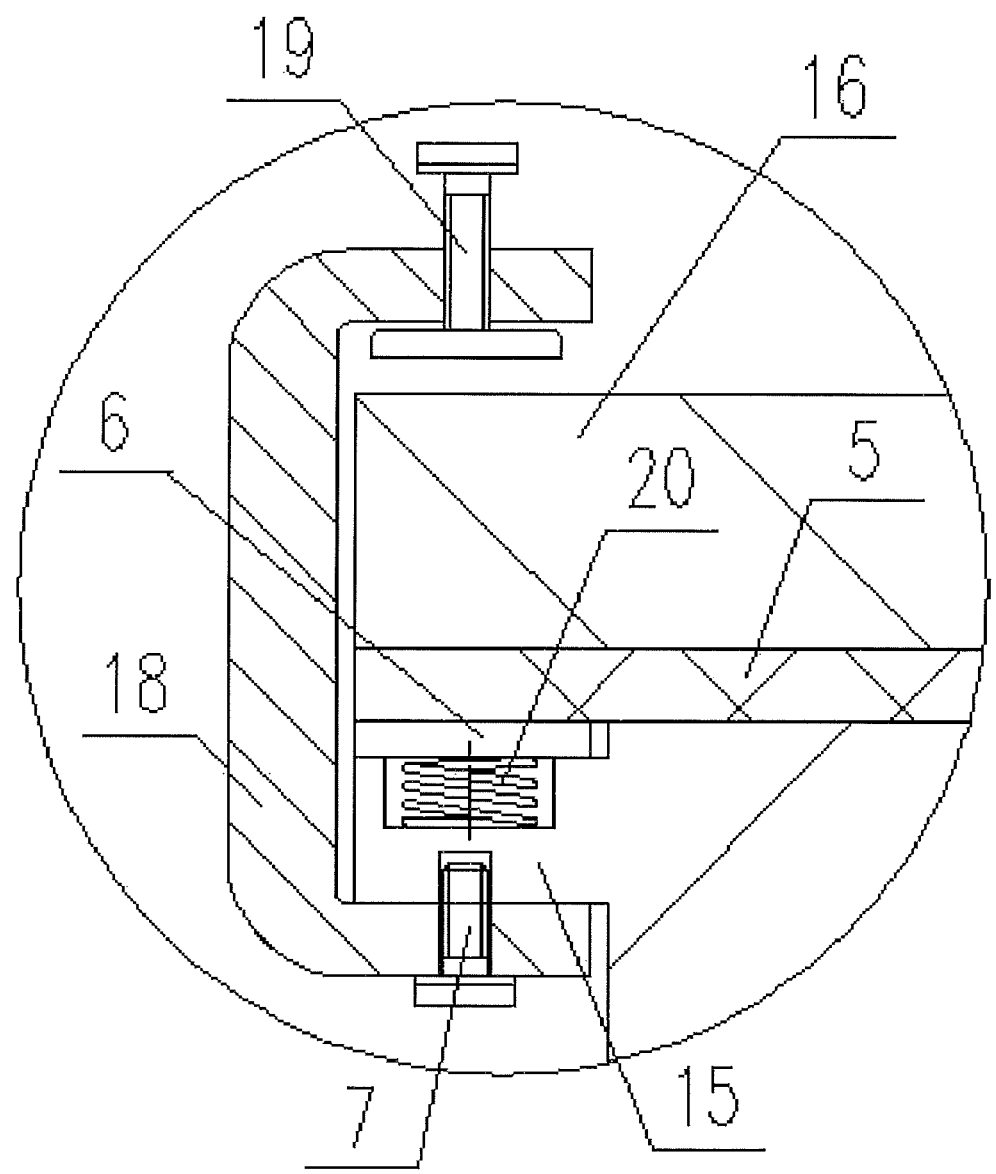
FIG. 4 is an enlarged diagram illustrating the spring position of FIG. 2.
Figure 5:
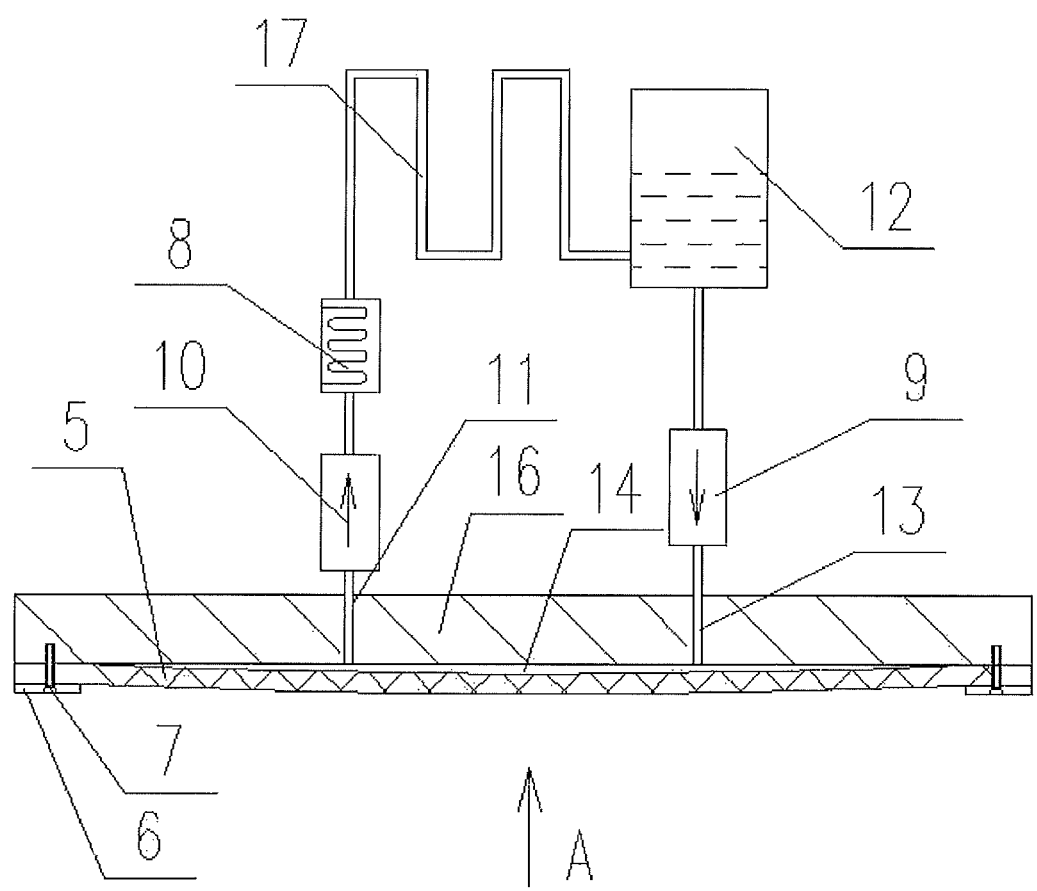
FIG. 5 shows a schematic diagram illustrating the circulation system in the first work state according to an embodiment of the present invention.
Figure 6:
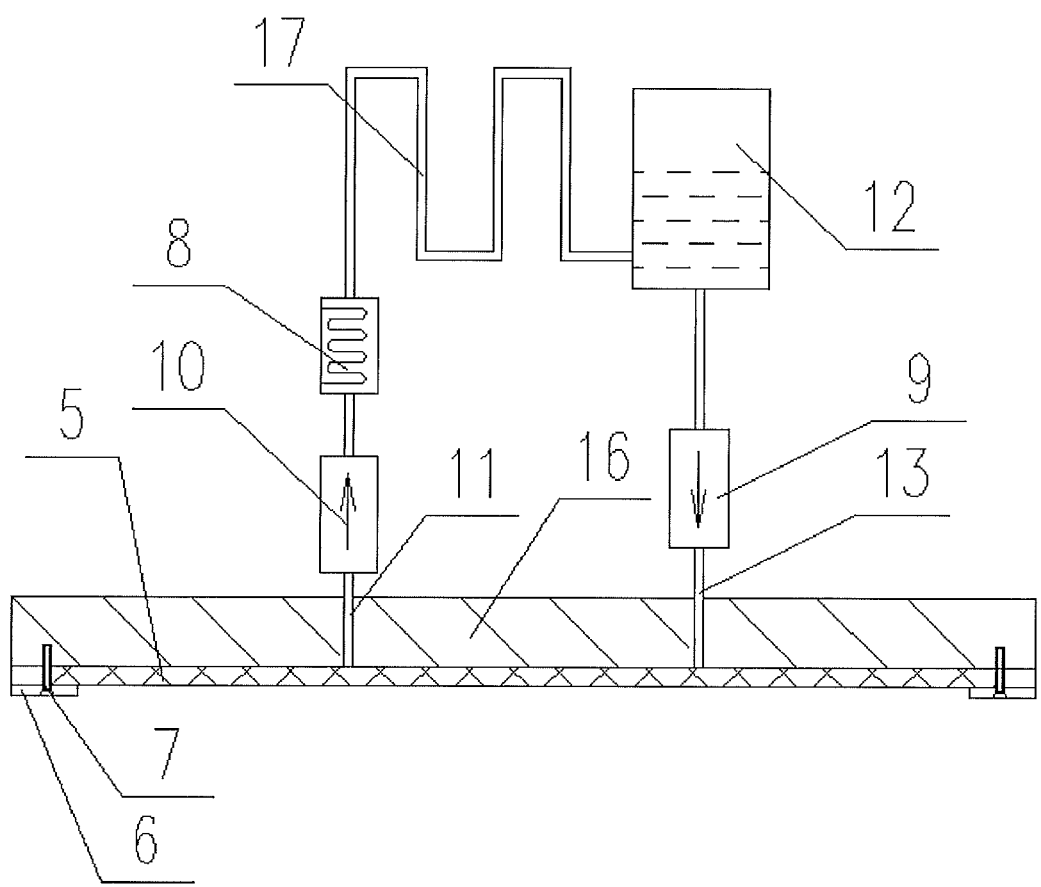
FIG. 6 shows a schematic diagram illustrating the circulation system in the second work state according to an embodiment of the present invention.

As shown in FIGS. 3 and 4, the circulation system stores water in the internal, including a cover plate 16, an elastic plate 5, a pressing compact ring 6, a water inlet 13, a check valve A 9, a self-pressing liquid storage tank 12, a check valve B 10, a water outlet 11, a pipeline 17 and a screw 7.

Figure 7:
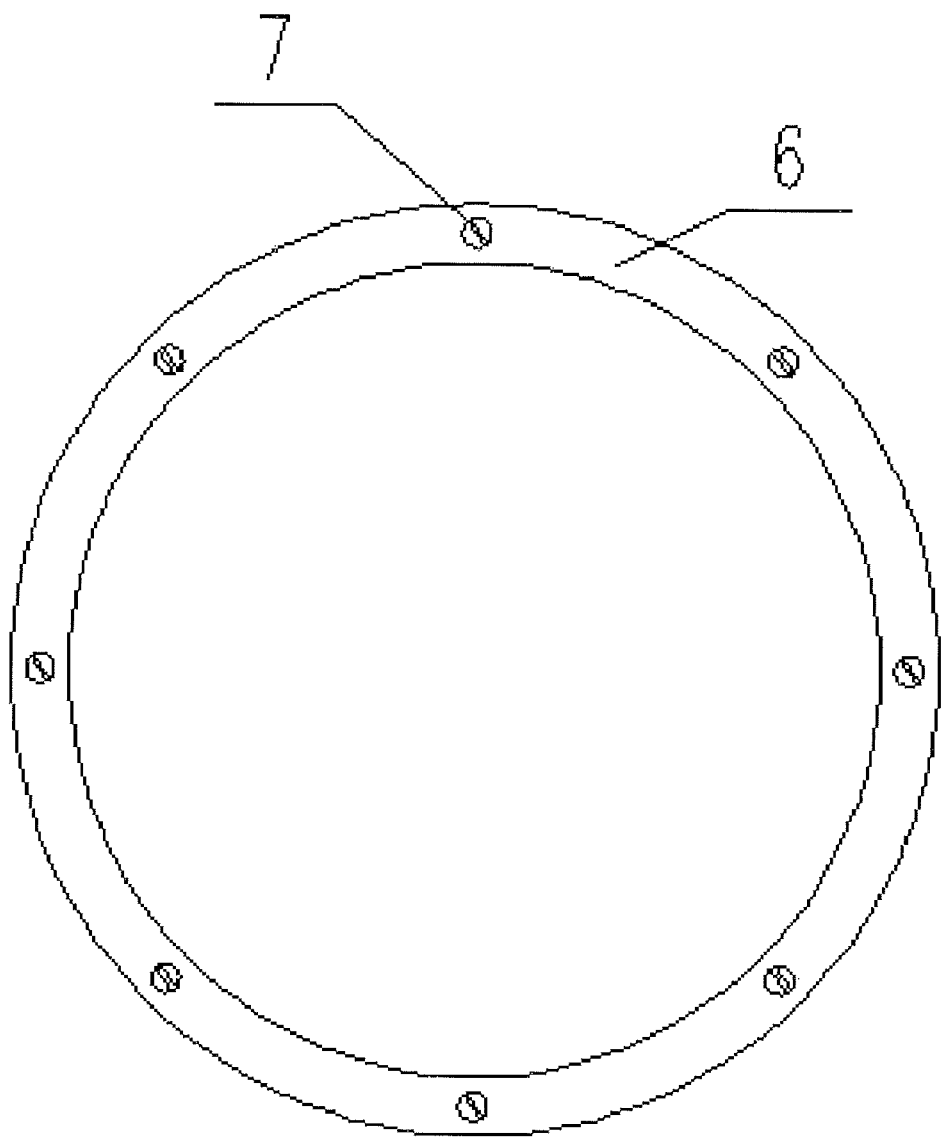
FIG. 7 is a narrowed diagram illustrating the direction A of FIG. 5.

The cover plate 16 is an iron product, the cover plate 16 and the elastic plate 5 are both in round shape, they are tightly fixedly connected at the entire edge of the circumference, the connection is that the pressing compact ring 6 is disposed on one side of the elastic plate 5 which is away from the cover plate 16, the pressing compact ring 6 and the elastic plate 16 and cover plate 16 are fixedly connected by the screw 7, as shown in FIG. 7. Because the cover plate 16 and the elastic plate 5 just are fixedly connected at the edge, and the elastic plate 5 has elasticity itself, thus when the water is pressed into the space between them, a reservoir space 14 will be formed. The size of the reservoir space 14 is depended on the elasticity and the area of the elastic plate 5.

Two through holes are provided on the cover plate 16, which are inserted into the water inlet 13 and the water outlet 11 respectively, and the seal between them and the cover plate 16 is well. The water is flowed into and flowed out the reservoir space 14 by the water inlet 13 and the water outlet 11.

The water inlet 13 is connected to the check valve A, the check valve A just allow the water to flow into the cover plate 16 side, and the water flowed from the cover plate 16 side is not enable to be passed. The water outlet 11 is connected to the check valve B, the check valve B just allow the water flowed from the cover plate 16 side to pass, the water flowed into the cover plate 16 is not enable to be passed. The self-pressing liquid storage tank 12 is connected to check valve A and check valve B by the pipeline 17 respectively. The above structure allows the self-pressing liquid storage tank 12 to press the water into the reservoir space 14 and the water in the reservoir space 14 is pressed into the self-pressing liquid storage tank 12 smoothly.

A heating pipe 8 is provided at the water outlet of the check valve B, the water in the circulation system will be kept in a certain temperature by the heating pipe 8. And the purpose of adjusting the water temperature is obtained by adjusting the heating pipe 8.

The space from the reservoir space 14 to the self-pressing liquid storage tank 12 including the whole pipeline 17 are all filled with water, the water in the self-pressing liquid storage tank 12 is not filled full of water, above the water surface is air. The role of the air is convenient to press the water into the self-pressing liquid storage tank smoothly due to be compressed, and provide the pressure for the water to be entered into the reservoir space 14 smoothly from the self-pressing liquid storage tank 12.

Figure 1:
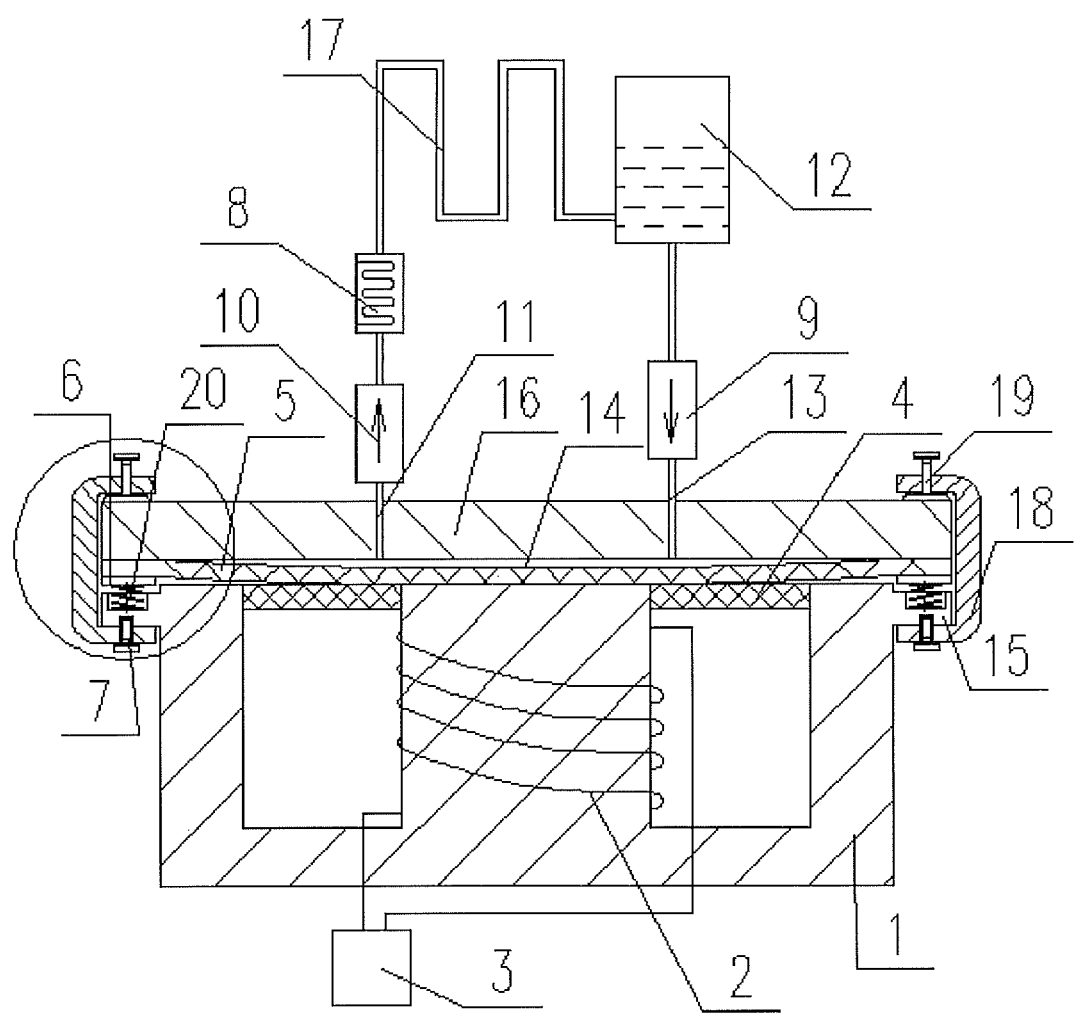
FIG. 1 shows a schematic diagram illustrating an embodiment in the first work state according to the present invention.
Figure 2:
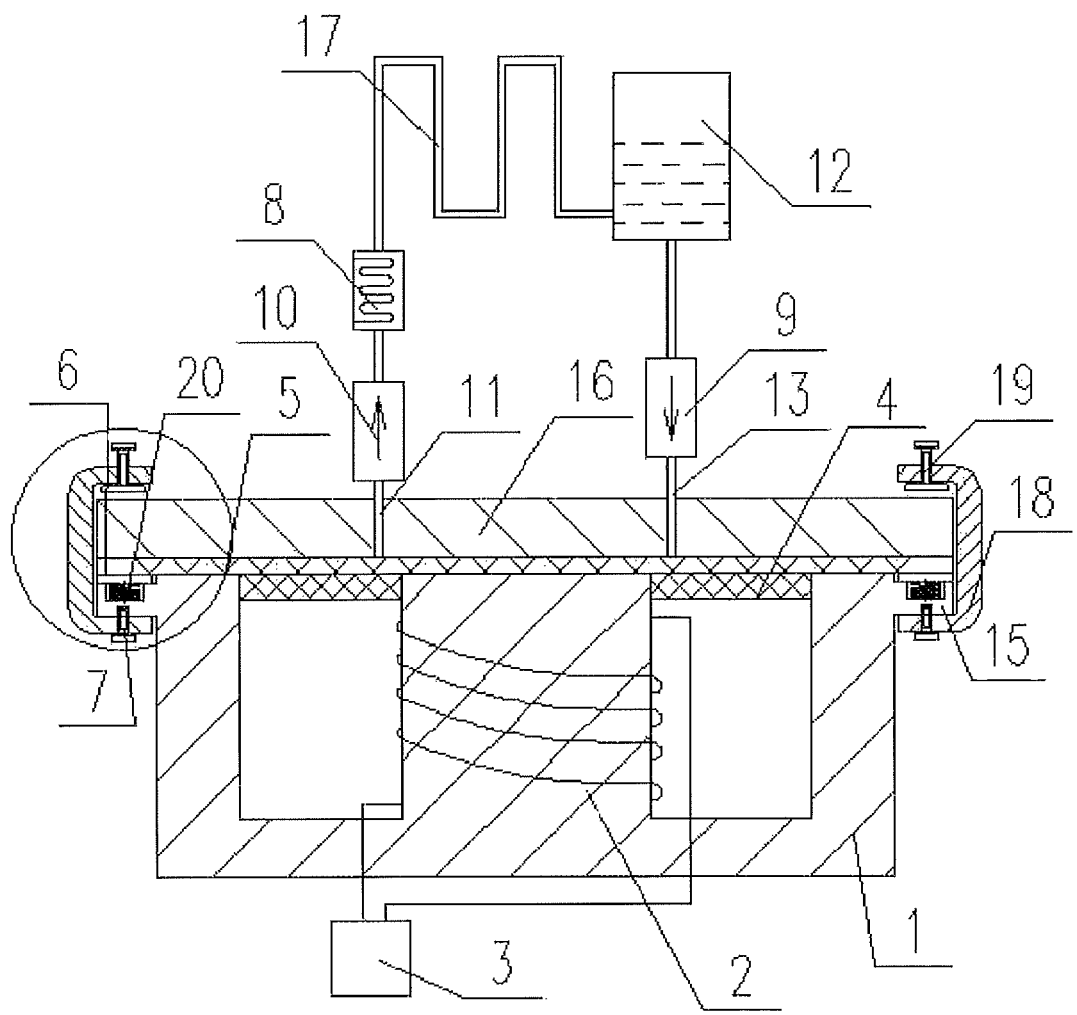
FIG. 2 shows a schematic diagram illustrating an embodiment in the second work state according to the present invention.

The power system as shown in FIGS. 1 and 2, which is provided at the underside of the circulation system, comprising a core 1, a coil 2, an insulation plate 4, a pulse power 3, a limit stop 18 and a limit screw 19.

The shape of core 1 is two concentric cylinders, in which the inner cylinder is solid which is located in the center of the outer cylinder, the outer cylinder is hollow, and the core 1 has an E-type cross-sectional shape.

The insulation plate 4 is in ring shape, the hole of the center of which is matched with the core 1. The insulation plate 4 is set in the top of the core 1 and connected with the core 1, the circumference of which is well sealed with the core 1. The upper surfaces of the insulation plate 4 and the core 1 are located in the same surface. In this manner, when fitting with the elastic plate 5, the water in the reservoir space 14 can be maximum extruded completely, thereby the circulation speed of the water is accelerated.

The Coil 2 is wound on the inner cylinder of the core 1, and the both ends of the coil 2 are connected to the pulse power 3. The coil 2 is isolated with the outside world by the insulation plate 4, which ensures its safety. When the pulse current supplied by the pulse power 3 is not equaled to zero, the inner cylinder of the core 1 generates magnetic line of force, the arrangement of the magnetic line of force forms a closed curve by the inner cylinder to pass through the cover plate 16 and the outer cylinder, as shown in FIG. 2, thereby the whole core generates the magnetic force, and it pass through the elastic plate 5 to generates an attraction to the cover plate 16, and then the cover plate 16 is fitted with the elastic plate 5; When the pulse current is equaled to zero, the magnetic line of force generated by the core 1 is disappeared, the core 1 which has lost the magnetic field releases the cover plate 16, and then the reservoir space 14 is formed between the cover plate 16 and the elastic plate 5.

Concave platforms 15 are provided at the edges of the entire circumference of the core 1, the concave platform 15 is adapted to the pressing compact ring 6, only the depth of the concave platform 15 is slightly less than the depth of the pressing compact ring 6. When the circulation system is placed on the power system, the pressing compact ring 6 is just placed on the concave platforms 15, At this moment, in the upper surface of the power system, that is, the top surface of the core 1 and the insulation plate 4 is just fitted with the elastic plate 5, and the pressure which circulation system suffers by the power system effects on the pressing compact ring 6. In this manner, the abrasion brought to the elastic plate 5 due to the core 1 has a continuous attract—loosen motion to the cover plate 16 can be reduced.

The circumferential direction connected by the circulation system and the power system provides with three limit stops 18, the section of the limit stop 18 has a groove profile, and the circumferential edge of the cover plate 16 and the concave platforms 13 is located in the groove profile. The bottom of the limit stop 18 is fixed on the underside of the concave platforms 15 by the screw 7, and the top of limit stop 18 is fixed on the top surface of the cover plate 16 by the limit screw 19, the limit screw 19 can adjust the displacement of the cover plate 16, while the amount of the displacement of the cover plate 16 may affect the amount of deformation of the elastic plate 5 and then affect the size of the reservoir space 14. The size of the reservoir space 14 is also affected by the size of the magnetic force. In this manner, a comfortable distance between the cover plate 16 and the concave platforms 15 can be obtained by adjusting the limit screw 19, which allows the cover plate 16 to perform a reciprocating smoothly when the core 1 has a continuous attract—loosen motion to the cover plate 16 within the comfortable space.

Three grooves are provided on the circumferential direction of the top surface of the concave platforms 15, a spring 20 is provided in each groove, as shown in FIG. 3, the length of the spring 20 in the natural state is larger than the depth of the grooves. In this manner, when the spring 20 is compressed, it will generate an elasticity to the pressing compact ring 6 located above thereof. When the electric current of the coil 2 is equaled to zero, the pressure suffered by the elastic plate 5 is removed, the spring 20 under the compress state starts to stretch and generates an elasticity on the pressing compact ring 6, as shown in FIG. 4, the cover plate 16 moves upward, and the water will continually flow into the reservoir space 14 with the movement of the cover plate 16.

When this embodiment under the normal state, the whole pipeline is filled with water, the cover plate and the elastic plate are not fitted each other, the reservoir space 14 is formed between them. When working, the pulse power 3 generates an nonzero pulse current first, the core 1 generates an attraction to the cover plate 16, thereby the elastic plate 5 and the cover plate 16 are gradually fitted each other, in the process of the fit, the reservoir space 14 gradually becomes smaller, and the pressure gradually becomes larger and then the water in it is pressed out, and flows through the check valve B 10 from the water outlet 11 to flows into the pipeline 17, and flows into the self-pressing liquid storage tank 12 finally. The air in the self-pressing liquid storage tank 12 is compressed to generate the pressure to the water, at this moment, the pulse current generated by the pulse power 3 becomes zero, the core 1 has no magnetic force and loosen the cover plate 16, the spring 20 stretches and generates an elasticity to the pressing compact ring, the cover plate 16 moves upward, due to the role of the check valve B, the water in the pipeline 17 only be passed through the check valve A to flow into the water inlet 13 under the air pressure and gravity itself, finally, flows back to the reservoir space 14 between the cover plate 16 and the elastic plate 5. Thus, one water cycle is completed. The pulse current is continually put through by the pulse power 3, the above water cycle is performed repeatedly.

Lengthening the pipeline 17 and wounded it in the blanket, pad, a new plumbing pad will be formed.

What is claimed is:

1. A heart-type circulation device, comprising a power system, a cover plate, an elastic plate, a pressing compact ring, water inlet, a check valve A, a self-pressing liquid storage tank, a check valve B, a water outlet and a pipeline; wherein the elastic plate is disposed above the power system, the pressing compact ring is disposed on a periphery of a bottom surface of the elastic plate, and the pressing compact ring, the elastic plate, and the cover plate are fixedly connected in sequence from bottom to top; the water inlet and the water outlet are lead to a space between the cover plate and the elastic plate through the cover plate respectively; the water inlet, the check valve A, the self-pressing liquid storage tank, the check valve B and the water outlet are connected in sequence by the pipeline, wherein the direction of the check valve A is the direction of the fluid flowing to the cover plate, and the direction of the check valve B is the direction of the fluid flowing out of the cover plate; a space in the whole pipeline and the self-pressing liquid storage tank is filled up with a liquid; the cover plate is made of magnetic material, the power system comprises a core, a coil, an insulation plate and a pulse power, wherein the coil is wound on the core, both ends of the coil are connected with the pulse power, and the insulation plate is disposed on the top of the core; when working, the pulse power supplies pulse current to the coil, and when the pulse current passes through the coil, the core will generate a magnetic field, the magnetic field passes through the elastic plate to attract the cover plate, thereby the elastic plate is fitted with the cover plate, and when the pulse current does not pass through the coil, the magnetic field of the core disappears, the space between the cover plate and the elastic plate will be formed.

2. The heart-type circulation device according to claim 1, wherein,
the self-pressing liquid storage tank is made of rigid material, and is filled up with the liquid, a space above surface of the liquid is filled up with air; or
the self-pressing liquid storage tank is made of elasticity material, and is filled up with the liquid.

3. The heart-type circulation device according to claim 2, wherein,
the heart-type circulation device further comprises a heating pipe which is connected with the pipeline.

4. The heart-type circulation device according to claim 3, wherein, a shape of the core is two concentric cylinders, wherein an inner cylinder is solid which is disposed on the center of a outer cylinder, and the outer cylinder is hollow, and the core has an E-type cross-sectional shape, the coil is wound on the inner cylinder; the insulation plate is an annulus, and a center hole of the insulation plate is matched with the core, the connection between both are sealed and their top surfaces are in same surface.

5. The heart-type circulation device according to claim 4, wherein a concave platform is disposed on a periphery of the core, the concave platform is adapted to the pressing compact ring; the power system further comprises several limit stops, a section of the limit stop has a groove profile, the cover plate and the concave platform are clipped in a groove, a bottom of the limit stop is fixed on a underside of the concave platform, a top of the limit stop disposes an adjustment screw.

6. The heart-type circulation device according to claim 5, wherein, a depth of the concave platform of the core is less than a thickness of the pressing compact ring.

7. The heart-type circulation device according to claim 5, wherein,
the heart-type circulation device further comprises several springs, which are disposed between the concave platform and the pressing compact ring.

8. The heart-type circulation device according to claim 1, wherein,
the check valve A and the check valve B are mechanical valves or solenoid valves.

* * * * *